United States Patent
Nir et al.

(10) Patent No.: US 7,030,062 B2
(45) Date of Patent: Apr. 18, 2006

(54) CONTROLLED RELEASE FORMULATIONS OF ANIONIC HERBICIDES

(75) Inventors: Shlomo Nir, Mazkeret Batya (IL); Baruch Rubin, Mazkeret Batya (IL); Yael Mishael, Rehovot (IL); Thomas Undabeytia, Seville (ES); Onn Rabinovitch, Kfar Yuval (IL); Tamara Polubesova, Rehovot (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 10/250,556

(22) PCT Filed: Jan. 3, 2002

(86) PCT No.: PCT/IL02/00004

§ 371 (c)(1),
(2), (4) Date: Dec. 9, 2003

(87) PCT Pub. No.: WO02/052939

PCT Pub. Date: Jul. 11, 2002

(65) Prior Publication Data

US 2004/0087447 A1    May 6, 2004

Related U.S. Application Data

(60) Provisional application No. 60/259,174, filed on Jan. 3, 2001.

(51) Int. Cl.
*A01N 47/36* (2006.01)

(52) U.S. Cl. ........................ 504/211; 504/214; 504/215; 504/227; 504/239; 504/273; 504/274; 504/275; 504/345; 504/359; 504/367

(58) Field of Classification Search ................. 504/211, 504/214, 215, 227, 239, 273, 274, 275, 345, 504/359, 367
See application file for complete search history.

(56) References Cited

U.S. PATENT DOCUMENTS

| 4,849,006 A | 7/1989 | Knudson, Jr. |
| 6,261,997 B1 * | 7/2001 | Rubin et al. ................. 504/148 |

FOREIGN PATENT DOCUMENTS

GB    1 565 362    4/1980

(Continued)

OTHER PUBLICATIONS

Mishael, Yael Golda, et al., "Sulfometuron Incorporation in Cationic Micelles Adsorbed on Montmorillonite", J. Agric. Food Chem., vol. 50, pp. 2856-2863, 2002.

(Continued)

*Primary Examiner*—S. Mark Clardy
(74) *Attorney, Agent, or Firm*—Nath & Associates PLLC; Viviana Amzel; Lee C. Heiman (57) ABSTRACT

A herbicidal formulation comprising of incorporating the herbicide in a micelle or vesicle and adsorbing said micelle or vesicle containing herbicide on clay mineral. The formulation is suitable in particular for negatively charged herbicides at pH above 6. The herbicidal formulation provides slow release and reduced leaching of the herbicide to deep soil layers, thus reducing contamination of underground water and soil. Furthermore, the herbicide is maintained in the target vicinity, thus its efficiency is enhanced and a smaller concentration may be used.

15 Claims, 5 Drawing Sheets

FOREIGN PATENT DOCUMENTS

WO      WO 98/08380      3/1998

OTHER PUBLICATIONS

Mishael, Yael Golda, et al., "Slow-Release Formulations of Sulfometuron Incorporation in Micelles Adsorbed on Montmorillonite". J. Agric. Food Chem., vol. 50, pp. 2864-2869, 2002.

Carter, A. D., "Herbicide movement in soils: principles, pathways and processes". Weed Res., vol. 40, pp. 113-122, 2000.

Dailey, Oliver D., Jr., et al., "Polymeric Microcapsules of the Herbicides Atrazine and Metribuzin: Preparation and Evaluation of Controlled-Release Properties". J. Agric. Food Chem., vol. 41, pp. 1517-1522, 1993.

El-Nahhal, Yasser, et al., "Leaching, Phytotoxicity, and Weed Control of New Formulations of Alachlor". J. Agric. Food Chem., vol. 46, pp. 3305-3313, 1998.

El-Nahhal, Yasser, et al., "Movement of metolachlor in soil: effect of new organo-clay formulations". Pestic. Sci., vol. 55, pp. 857-864, 1999.

El-Nahhal, Yasser, et al., "Montmorillonite-Phenyltrimethylammonium Yields Environmentally Improved Formulations of Hydrophobic Herbicides". J. Agric. Food Chem., vol. 48, pp. 4791-4801, 2000.

El-Nahhal, Yasser, et al., "Organo-Clay Formulation of Acetochlor for Reduced Movement in Soil". J. Agric. Food Chem., vol. 49, pp. 5364-5371, 2001.

Ferraz André, et al., "Controlled Release of 2,4-D from Granule Matrix Formulations Based on Six Lignins". J. Agric. Food Chem., vol. 45, pp. 1001-1005, 1997.

Gerstl, Z., et al., "Controlled Release of pesticides into Water from Clay-Polymer Formulations". J. Agric. Food Chem., vol. 46, pp. 3803-3809, 1998.

Gish, T. G., et al., "Field-Scale Mobility and persistence of Commercial and Starch-Encapsulated Atrazine and Alachlor". J. Environ. Qual., vol. 23, pp. 355-359, 1994.

Harvey, John, Jr., et al., "Properties of Sulfometuron Methyl Affecting Its Environmental Fate: Aqueous Hydrolysis and Photolysis, Mobility and Adsorption on Soils, and Bioaccumulation Potential". J. Agric. Food Chem., vol. 33, pp. 590-596, 1985.

Loukas, Yannis, L., et al., "γ-Cyclodextrin Inclusion Complex of a New Organophosphorus Insecticide. Determination of Stability Constant with HPLC". J. Agric. Food Chem., vol. 42, pp. 944-948, 1994.

Pool, C. F., et al., "Leaching depth of imazamethabenz methyl and chlorsulfuron + metsulfuron methyl in different soils". Applied Plant Sci., vol. 9, pp. 43-47, 1995.

Sarmah, Ajit K., et al., "Fate and behaviour of triasulfuron, metsulfuron-methyl, and chlorsulfuron in the Australian soil enviroment: a review". Aust. J. Agric. Res., vol. 49, pp. 775-790, 1998.

Veeh, R. H., et al., "Transport of Chlorsulfuron through Soil Columns". J. Environ. Qual., vol. 23, pp. 542-549, 1994.

* cited by examiner

HDTMA

ODTMA

DDAB

SULFOMETURON

SULFENTRAZONE

IMAZAQUIN

DDOB

SULFOSULFURON

CONTROLLED RELEASE FORMULATIONS OF ANIONIC HERBICIDES

This application claims benefit of Provisional Application No. 60/259,174, filed Jan. 3, 2001.

FIELD OF THE INVENTION

This invention relates to herbicidal formulations. In particular, it relates to controlled release herbicidal formulations aimed at reducing ground water and soil contamination and yielding higher efficiency of the applied herbicide.

BACKGROUND OF THE INVENTION

The following is a list of references, which is intended for a better understanding of the background of the present invention.

Carter, A. D. Herbicide movement in soil: principles, pathways and processes. *Weed Res.* 2000, 40, 113–122.

Dailey, O. D.; Dowler, C. C.; Mullinix, B. G. Polymeric microcapsules of the herbicides atrazine and metribuzin; preparation and evaluation of controlled-release properties. *J. Agric. Food Chem.* 1993, 41, 1517–1522.

El Nahhal, Y.; Nir, S.; Polubesova, T.; Margulies, L.; Rubin, B. Leaching, phytotoxicity, and weed control of new formulations of alachlor. *J. Agric. Food Chem.* 1998, 46, 3305–3313.

El Nahhal, Y; Nir, S.; Polubesova, T.; Margulies, L.; Rubin, B. Movement of metolachlor in soil: Effect of new organo-clay formulations. *Pestic. Sci.* 1999, 55, 857–864.

El Nahhal, Y.; Nir, S.; Serban, C.; Rabinovitch O.; Rubin, B. Montmorillonite-Phenyltrimethylammonium Yields Environmentally Improved Formulations of Hydrophobic Herbicides. *J Agric. Food Chem.* 2000, 48, 4791–4801.

El Nahhal, Y.; Nir, S.; Serban, C.; Rabinovitch O.; Rubin, B. Organo-clay formulations of acetochlor for reduced movement in soil. *J Agric. Food Chem.* 2001, 49, 5364–5371.

Ferraz, A.; Souza, J. A.; Silva, F. T.; Goncalves, A. R.; Bruns, R. E.; Cotrim, A. R.; Wilkins, R. M. Controlled release of 2,4-D from granule martix formulations based on six lignins. *J. Agri. Food Chem.* 1997, 45, 1001–1005.

Gerstl, Z.; Nasser, A.; and Mingelgrin, U. Controlled release of pesticides into water from clay-polymer formulations. *J Agric. Food Chem.* 1998, 46, 3803–3809.

Gish, T. G.; Shirmohammada, A.; Wienhold, B. J. Field scale mobility and persistence of commercial and starch encapsulated atrazine and alachlor. *J. Environ. Qual.* 1994, 23, 355–359.

Harvey, J.; Dulka, J.; Anderson, J. J. Properties of sulfometuron methyl affecting its environmental fate: aqueous hydrolysis and photolysis, mobility and adsorption on soils, and bioaccumulation. *J Agric. Food Chem.* 1985, 33, 590–596.

Loukas, Y. L.; Antoniadou-Vyza, E.; Papadaki-Valiraki, A.; Machera, K. G. g-Ciclodextrin inclusion complex of a new organophosphorus insecticide. Determination of stability constant with HPLC. *J Agric. Food Chem.* 1994, 42, 944–948.

Pool, C. F.; Du-Toit, D. Leaching depth of imazamethabenz methyl and chlorsulfuron and metsulfuron methyl in different soils. *Applied Plant Sci.* 1995, 9, 43–47.

Sarmah, A. K.; Kookana, R. S.; Alston, A. M. Fate and behavior of trisulfusulfiron, metsulfuron-methyl, and chlorsulfiron in Australian soil environment: a review. *Austr. J. Agric. Res.* 1998, 49, 775–790.

Veeh, R. H.; Inskeep, W. P.; Roe, F. L.; Ferguson, A. H. Transport of chlorsulfuron through soil columns. *J. Environ. Qual.* 1994, 23, 542–549.

Use of agrochemicals, despite health and environmental problems associated with their use, is essential for producing the required amount of food, worldwide. One of the problems associated with their use stems from their mode of application. In order to achieve a pronounced effect, high doses of agrochemical are used in order to compensate for the fact that part of the agrochemical is "lost" to the environment. One mechanism of "losing" agrochemicals, and in particular, herbicides, is by leaching and surface migration. These mechanisms lead to a reduction in the efficacy of the applied herbicide leading ultimately to higher doses of herbicide that are costly both economically and environmentally. One of the environmental problems is associated with surface and groundwater contamination (Carter, 2000).

Slow and controlled release formulations aimed at prolonging the effect of the herbicide and inhibiting its migration to deeper layers of the soil were developed. These include, encapsulation using alginate (Gerstl et al. 1998), cyclodextrin complexes (Loukas et al. 1994), formulations with lignin (Ferraz et al. 1997), formulations with starch (Gish et al. 1994), formulations with organo-clay (El-Nahhal et al. 2000, 2001) and polymer capsulation (Dailey et al. 1993). It should however be noted that such formulations are specifically designed for hydrophobic herbicides. Anionic herbicides such as the sulfonylureas, imidazolinones and triazolopyrimidines can not be formulated as described above. Such anionic herbicides are weak acids and are negatively charged at moderate basic pH. In calcareous soils having a basic pH, these negatively charged herbicides leach to deep soil layers and migrate to non-target layers (Veeh et al. 1994; Pool et al. 1995; and Sarmah et al. 1998). Thus, despite the fact that these herbicides are very useful, their interaction with the environment renders their use inefficient, and higher doses than actually would be needed are applied in order to achieve the desired effect. Consequently, there is a need to provide efficient formulations of herbicides that are weak acid herbicides and are negatively charged at the pH of the soil they are applied into.

SUMMARY OF THE INVENTION

The present invention is based on the fact that negatively charged herbicides may be formulated into suitable formulations enabling their slow and controlled release.

Thus the present invention is directed to a herbicidal formulation comprising of incorporating a herbicide in micelles or vesicles and adsorbing said micelles or vesicles containing herbicide on a clay mineral. The herbicide is negatively charged at pH above 6. In particular the herbicide is selected from the group comprising of sulfonylureas, imidazolinones, aryltriazinones triazolopyrimidines or their mixtures. The micelles are positively charged being composed of charged organic cation having large hydrophobic moieties in their structure. Preferably the micelles are quaternary amine cation micelles selected of the formula $(CH_3)_3 N^+(CH_2)_n—CH_3$, n being from 15 to 20. The vesicles are positively charged and are chosen from the group comprising of lipids. The clay mineral is negatively charged. Typically it may be chosen from smectites of which montmorillonite is one member and sepiolite.

The invention is further directed to use of a herbicidal formulation for efficiently controlling undesired vegetation. The formulation comprises a negatively charged herbicide at pH above 6 incorporated in micelles or vesicles and adsorbing the micelles or vesicles on a clay mineral. The micelles are positively charged being composed of positively charged organic cation having large hydrophobic moieties in their structure. Preferably the micelles are quaternary amine cation micelles selected of the formula $(CH_3)_3N^+(CH_2)_n$—$CH_3$, n being from 15 to 20. The vesicles are positively charged and are chosen from the group comprising of lipids. The clay mineral is negatively charged; it may be chosen from sepiolite and smectites of which montmorillonite is one member.

The invention is additionally directed to a method of controlling undesirable vegetation by applying the herbicidal formulation of the invention to the undesired vegetation or to its vicinity. The herbicides that may be formulated are sulfonylureas, imidazolinones, aryltriazinones triazolopyrimidines or their mixtures. The herbicidal formulation reduces the leaching of the herbicide to deeper soil, thus contamination of underground water is reduced.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
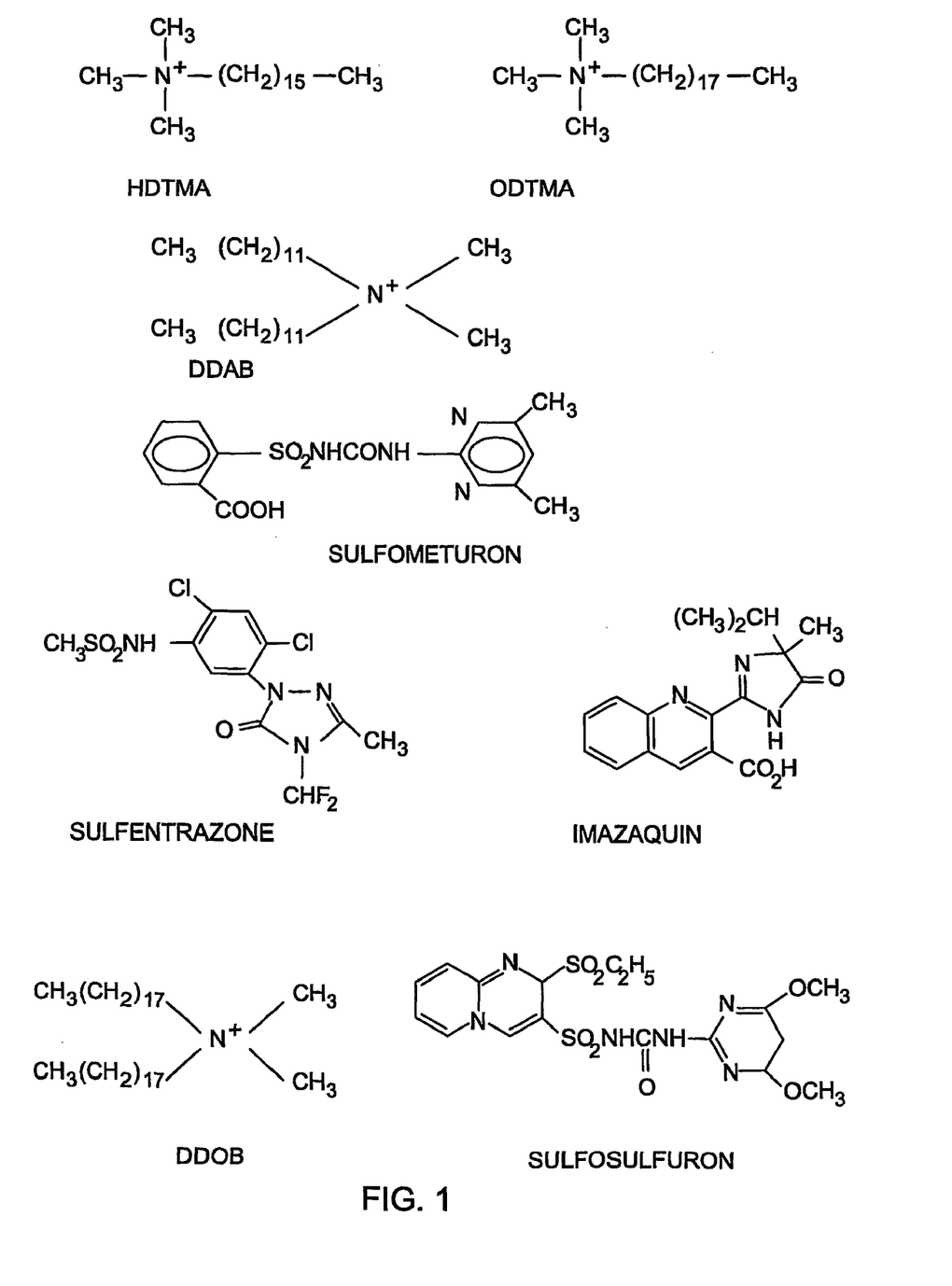
FIG. 1 shows the chemical formulae of the compounds described in the invention.

As mentioned above the present invention is directed to herbicidal formulations suitable for negatively charged herbicides. Negatively charged herbicides are very poorly adsorbed in most agricultural soils due to the fact that above pH 6 they are in their anionic form. The herbicidal formulations are based on the incorporation of the herbicide into positively charged micelles or vesicles and adsorbing the herbicide-micelles or -vesicles onto a negatively charged clay mineral. The positively charged micelles are being composed of charged organic cation having large hydrophobic moieties in their structure. Preferably the micelles are quaternary amine cation micelles selected of the formula $(CH_3)_3N^+(CH_2)_n$—$CH_3$, n being from 15 to 20. Non-limiting examples may be hexadecyltrimethylammonium (HDTMA) or octadecyltrimethylammonium (ODTMA). Vesicles are composed of positively charged lipids, such as didodecyldimethylammonium bromide (DDAB) or dioctadecyldimethylammonium bromide (DDOB). The micelle or vesicle containing herbicide, in turn are adsorbed on a negatively charged clay mineral. The anionic herbicides are chosen from the sulfonylureas, imidazolinones, triazolopyrimidines, aryltriazinones among other groups. FIG. 1 shows chemical formulae of several of the compounds used in the present invention. The clay mineral may be chosen from smectites from which montmorillonite is one preferred member or sepiolite. An optimal formulation for the herbicide that would maintain its activity should take into account two factors. Initially, the herbicide-micelle (or vesicle)-clay system should be designed such as to obtain efficient adsorption of the herbicide in the micelle (or vesicle)-clay system. Such an adsorption of the herbicide yields its slow release and reduced leaching, whereas leaching of the herbicide in commercial formulations leads to its significant loss to the ground. Thus, on one hand the formulation should secure the herbicide in the formulation despite environmental factors. On the other hand the formulation should enable slow desorption of the herbicide from the micelle (or vesicle)-clay system while maintaining its biological activity, i.e. the herbicide is not altered. Desorption studies of sulfometuron (SFM), sulfosulfuron (SFS) and sulfentrazone (SFZ) from the formulations into water showed a low desorption rate after one day. Thus the herbicidal formulation of the present invention may be regarded as a controlled release formulation.

An efficient formulation is determined, among other factors, by its high biological activity at the root zone, and little activity at depths where no biological activity is needed and the herbicide can only cause harm by leaching and contaminating ground water. In the present invention reduction of leaching of the formulated herbicide was shown in soil columns. Plant bioassay, by measurements of root elongation, demonstrated the biological efficacy of the formulated herbicide. Thus, as presented in the accompanying examples, the herbicidal formulation of the present invention exhibits better herbicidal activity and less leaching compared to commercial water dispersible-granule formulation (OUST™ Dupont). Such a formulation therefore enables a controlled, slow release mechanism leading to the use of a smaller amount of herbicide and the small amount is more effective since it is more concentrated at the main site of uptake due to diminished leaching to deeper layers.

EXAMPLES & DESCRIPTION

Example 1

Preparation of Sulfometuron, Sulfentrazone, Imazaquin and Sulfosulfuiron—Octadecyltrimethylammonium.

Sulfometuron (SFM) was prepared in a buffer solution (pH 8.5–9) of 70% 0.05M sodium tetraborate-10-hydrate and 30% 0.1M HCl. Alternatively, Tris buffer at pH 8.5–9 may be used to prepare SFM-micelle solutions having the same percent of SFM adsorbed on clay. Sulfosulfuron (SFS)-micelle solutions were prepared in a Tris buffer at pH 7–7.5. Water solutions of sulfentrazone (SFZ) and imazaquin (IMQ) were used. Herbicide and octadecyltrimethylammonium (ODTMA) solutions were prepared by first adding herbicide to the buffer or water solutions, and then adding a desired amount of ODTMA to the solution. The various concentrations of added ODTMA are displayed in Table 1.

TABLE 1 herbicide-micelle-clay formulations

| Clay added (g/L) | ODTMA added (mM) | Herbicide added (mM) | Notation of formulation | Active ingredient (w/w %) |
|---|---|---|---|---|
| Sulfometuron | | | | |
| 2.5 | 2.5 | 0.125 | 2.5/2.5/0.125 | 1.6 |
| 5 | 5 | 0.25 | 5/5/0.25 | 1.6 |
| 5 | 5 | 0.25 | 5/5/0.25[a] | 1.6 |
| 5 | 5 | 0.05 | 5/5/0.05 | 0.32 |
| Sulfosulfuron | | | | |
| 5 | 5 | 0.25 | 5/5/0.25 | 2.30 |
| 5 | 5 | 0.05 | 5/5/0.05 | 0.46 |
| Sulfentrazone | | | | |
| 2 | 2.5 | 0.043 | 2/2.5/21.5[b] | 0.8 |
| 2 | 2.5 | 0.069 | 2/2.5/34.4 | 1.3 |
| 2 | 2.5 | 0.086 | 2/2.5/43 | 1.65 |
| 2 | 2.5 | 0.138 | 2/2.5/68.87 | 2.66 |
| 2 | 5 | 0.086 | 2/5/43 | 1.65 |
| 2 | 10 | 0.086 | 2/10/43 | 1.65 |
| Imazaquin | | | | |
| 2 | 2.5 | 0.054 | 2/2.5/26.77[b] | 0.56 |
| 2 | 2.5 | 0.107 | 2/2.5/53.53 | 1.01 |
| 10 | 12 | 0.107 | 10/12/53.53 | 1.17 |

[a]The formulation (5 g/L) was washed with water.
[b]In these cases the notation implies that the third number (e.g. 21.5) denotes μmol ai/g clay added.

Example 2

Preparation of a SFM, SFS, SFZ IMQ-ODTMA-clay Formulations

Solutions of herbicide and ODTMA at different concentrations (10 ml) were added to different clay concentrations (5 ml) in 40 ml polycarbonate centrifuge tubes, reaching a final volume of 15 ml. The final concentrations of SFM and SFS were 0.05–0.5 mM, those of ODTMA were 0.25–12 mM and 0.25–10 g clay/L. The final concentrations of IMQ and SFZ were 21.5–68.87 μmol/g and those of ODTMA were 2.5–12 mM, and 2–10 g clay/L (Table 1). The suspensions were kept under continuous agitation for 3 days (1 day for SFZ), reaching equilibration. Supernatants were separated by centrifugation at 15,000 g for 30 min and herbicide concentration was measured. The final concentrations of formulations and the weight percent of the herbicides in the formulation are shown in Table 1. Formulation 5/5/0.25 of SFM was washed at a clay concentration of 5 g/L (formulation 5/5/0.25 w), in order to release the SFM molecules that were loosely bound, but the percent of SFM desorbed was low (Table 2a) indicating that there was no significant difference in SFM loading between the two formulations.

Example 3

Preparation of SFM-didodecyldimethyl-Ammonium Bromide-clay formulations

A 0.6 mM SFM in buffer was added to 6 mM didodecyldimethyl-ammonium bromide (DDBM). The combined solution was mixed with montmorillonite in polypropylene tubes, the final concentration of the clay being 1.6 g/L or 3.6 g/L. The final concentration of SFM in the vesicles (determined in a manner as described in Example 2) was 6.1% and 4.9% for the 1.6 g/L and 3.6 g/L, respectively.

Example 4

Release of the Herbicides from the ODTMA-clay Formulations

Desorption of SFM was detected for a period beginning 20 min after initiation of the desorption up to nine days. Desorption of SFS was measured after one day. Desorption of SFZ was measured after 10 min. up to 24 hours. Desorption is initiated by replacing the supernatants with water at different clay concentrations. Subsequently supernatants were separated by centrifugation and the desorbed herbicide was measured. SFM desorption from the formulations in water was usually measured after one day at different clay concentrations (Table 2a). Results of SFZ are summarized in Table 2b.

TABLE 2a

Adsorption and desorption of SFM and SFS from different clay-micelle formulations.

| Clay (g/L) | ODTMA (mM) | Herbicide (mM) | SEM Adsorbed (%) | SFM desorbed (%) after 1 day[a] | | | | | Clay conc. (g/L) |
|---|---|---|---|---|---|---|---|---|---|
| SFM adsorption | | | | SFM desorption | | | | | |
| 0.25 | 0.25 | 0.05 | 9.4 | nd | | | | | 10 |
| 2.5 | 2.5 | 0.125 | 91.9 | 0.8 | | | | | 10 |
| 2.5 | 2.5 | 0.25 | 85.7 | 1.3 | | | | | 10 |
| 1.6 | 2.5 | 0.25 | 82.4 | 12.7 | | | | | 1.6 |
| 1.6 | 5 | 0.5 | 52.9 | 15.6 | | | | | 1.6 |
| 5 | 5 | 0.25 | 95.3 | 20 min | 1 h | 24 h | 48 h | 9 d | 10 |
| | | | | 0.4[b] | 0.6[b] | 0.5[b] | 0.5[b] | 0.5[b] | |
| | | | | | | 2.1 | | | 5 |
| | | | | | | 13.2 | | | 0.3 |
| 5 | 5 | 0.05 | 94.6 | 1.1 | | | | | 5 |
| 5 | 8 | 0.25 | 93.5 | 2.3 | | | | | 5 |
| 10 | 8 | 0.5 | 92.3 | 7.8 | | | | | 10 |
| 10 | 10 | 0.5 | 95.7 | 3.0 | | | | | 10 |
| 10 | 12 | 0.5 | 95.9 | 1.2 | | | | | 10 |

TABLE 2a-continued

Adsorption and desorption of SFM and SFS from different clay-micelle formulations.

| Clay (g/L) | ODTMA (mM) | Herbicide (mM) | SEM Adsorbed (%) | SFM desorbed (%) after 1 day[a] | Clay conc. (g/L) |
|---|---|---|---|---|---|
| SFS adsorption | | | | SFS desorption | |
| 5 | 5 | 0.25 | 98.0 | 0.6 | 5 |
| 5 | 5 | 0.05 | 97.2 | 1.3 | 5 |

[a]The standard deviations obtained for SFM adsorption and desorption range between 0.1 and 1.0%; nd indicates not detected.
[b]The concentrations measured are at the HPLC limit of detection.

TABLE 2b

Adsorption and desorption of SFZ from different clay-micelle formulations (2/2.5).

| Desorption time | Sulfentrazone added, μmol/g | Sulfentrazone adsorbed, μmol/g | Sulfentrazone desorbed, μmol/g | Sulfentrazone desorbed (%) from adsorbed |
|---|---|---|---|---|
| 10 min | 34.44 | 34.34 | 0.2 | 0.58 |
| 2 h | 34.44 | 34.34 | 0.14 | 0.42 |
| 8 h | 34.44 | 34.34 | 0.12 | 0.35 |
| 24 h | 34.44 | 34.34 | 0.1 | 0.29 |
| 10 min | 43 | 42.66 | 0.29 | 0.67 |
| 2 h | 43 | 42.66 | 0.22 | 0.52 |
| 8 h | 43 | 42.66 | 0.2 | 0.47 |
| 24 h | 43 | 42.66 | 0.16 | 0.38 |
| 10 min | 68.87 | 68.67 | 2.0 | 2.9 |
| 2 h | 68.87 | 68.67 | 1.96 | 2.85 |
| 8 h | 68.87 | 68.67 | 1.58 | 2.2 |
| 24 h | 68.87 | 68.67 | 0.73 | 1.1 |

The largest standard deviations obtained for SFZ adsorption and desorption were 2.75 and 0.005 μmol/g, respectively.

Example 5

Herbicide Analysis

All supernatants were filtered with Teflon filters (ISI, Petach Tikva, Israel) of 0.2 μm pore diameter. The herbicides were analyzed by HPLC (Merck Hitachi 6200, Tokyo, Japan) equipped with PDA detector. The reverse phase column was LiChrospher 100 RP-18 (5 mM (Merck, Darmstadt, Germany). The flow rate was 1.0 mL min$^{-1}$. The mobile phases were: for SFM, SFS and SFZ acetonitrile and water with 0.65 mM trifluoroacetic acid, 70:30 for SFM and SFS, 50:50 for SFZ; the mobile phase for IMQ was 60% methanol and 40% water. The wavelengths were set at 232 nm for SFM, 216 nm for SFS, 220 nm for SFZ and 242 nm for IMQ. The presence of the cations did not cause any interference with herbicide detection.

Relating to the results displayed in Table 2a it can be seen that for a clay concentration of 0.25 g/L, and a concentration of 0.05 mM SFM, adding ODTMA at a concentration close to the critical micelle concentration (0.25 mM), results in the adsorption of only 9.4% of the added SFM. This is due to the fact that there are only monomers in the system. However, upon adding 5 mM ODTMA while maintaining the SFM concentration, 94.6% of the SFM were adsorbed, due to the fact that SFM adsorbs on the clay due to its incorporation in micelles.

An additional conclusion is that enhancing SFM adsorption may be done by an increase in the clay concentration, but up to a certain limit, in order to avoid micelle decomposition. As can be seen in Table 2a, increasing the clay concentration from 1.6 g/L to 2.5 g/L and further to 5 g/L increased the percent of adsorbed SFM. At a concentration of 2.5 mM ODTMA increasing clay concentration from 1.6 g/L to 2.5 g/L increased SFM adsorption from 82.4% to 85.7%. At a concentration of 5 mM ODTA, increasing the clay concentration from 1.6 g/L to 5 g/L increased SFM adsorption from 52.9 to 95.3%, the increase in clay concentration and decrease in SFM concentration (0.5 to 0.25 mM), which partially due to enables a larger fraction of SFM to be bound to the micelles. An additional increase in the clay concentration to 10 g/L with higher ODTMA concentrations did not significantly increase the SFM adsorption, as expected, since the maximal SFM adsorption was already reached. SFS adsorbed at a very high level 97–98% of the amount added. The small percent of desorption, 0.6–1.3%, (Table 2b) shows the high affinity of the herbicide to the micelle-clay system. As expected, the percent of SFM desorbed (0.5–13.2%) decreased as the clay concentration in the solution increased (0.3–10 g/L) (Table 2a). A small percent of SFM desorbed even at a very low clay concentration, which may resemble its concentration at the top of the soil following irrigation. Consequently, such formulations have a potential for slow release. Results of adsorption and desorption percentages of SFM from vesicle-clay formulations are given in Table 3.

TABLE 3

Adsorption and desorption (%) of SFM from vesicle-clay formulations.

| Clay conc. g/L | Surfactant (mM) | SFM (mM) | Adsorbed SFM (%) | Desorbed (% of adsorbed SFM) |
|---|---|---|---|---|
| 1.6 | DDAB, 6 | 0.6 | 59.1 | 20.0 |
| 3.6 | DDAB, 6 | 0.6 | 84.6 | 9.5 |
| 1.6 | DDOB, 6 | 0.6 | 19.0 | 49.2 |
| 3.6 | DDOB, 6 | 0.6 | 37.0 | 38.3 |

The desorption of SFM from the 5/5/0.25 formulation at a relatively higher clay concentration, 10 g clay/L, was also measured after 20 min, 1, 24, 48 hours and 9 days by using separate tubes for each sample, or by discarding the supernatant each time and adding water for the next release. This last method is closer to the situation in the soil, where the leached herbicide is washed out. In both methods a small percent of the herbicide was released (±0.5%) (Table 2). The concentration of SFM measured in the supernatant was at the HPLC detection limit.

Relating to the results shown in Table 2b the highest adsorption of SFZ was found for 2/2.5 formulations: 99% of SFZ was adsorbed at 21.5, 43 and 68.87 µmol/g added; 78.5% for formulation 2/5 and 70% for formulation 2/10 were adsorbed at 43 µmol/g added. Lower adsorption for the last two complexes can be explained by higher loading of ODTMA on the surface of montmorillonite, when organic cations interact between themselves by hydrophobic binding and interact to a lesser extent with the herbicide. Adsorption of SFZ on pure montmorillonite was insignificant, 0.014% of the herbicide was adsorbed at 43 µmol/g of SFZ added. Adsorption of SFZ for 2/5/43 and 2/10/43 formulations were 33.76 and 30.23 µmol/g (78.5 and 70.3%) from the added amount.

Desorption by distilled water for 24 hours was 0.3% from the 2/2.5/43 SFZ formulation.

Adsorption of IMQ for 2/2.5/26.77, 2/2.5/53.53 and 10/12/53.53 formulations was 18.49, 33.71 and 37.52 µmol/g (69.2, 63 and 70.1% from added).

Example 6

Leaching in Soil Columns

Two soils were used for an analytical test and for a plant bioassay. The soil from each source was used after being dried and passed through a 2 mm sieve.

A. Soil from the upper horizon of a Typic Xeropsamment soil from Coria, Seville, Spain having the following properties: pH 8.0, carbonate content 6.9%, organic matter content 0.92%, sand 87.5%, silt 4%, clay 8.5%.

B. Soil from the top 30 cm of a sandy loam soil at the Faculty of Agriculture Experimental Farm in Rehovot, Israel having the following properties: pH of the soil is 7.5, carbonate content 0.0%, organic matter content 0.2%, sand 95.5%, silt 3.3% and clay 1.2%.

Analytical tests: Columns comprising of soil from two sources, Seville, Spain and Rehovot, Israel were prepared. Metacrylate tubes of 3.0 cm diameter were cut into 4- and 8-cm sections, and five units of 4 cm were glued together with a 8 cm unit at one end to construct a 28 cm column. The column was covered at the end opposite to the 8 cm unit with 1 mm nylon screen padded with a thin layer of glass wool (0.5 g) to hold the soil firmly in the column. The soil (0.246 kg) was packed from the top of the column (8 cm section), creating a 24 cm soil column that could be readily separated into 4 cm segments. A thin layer of glass wool was placed on top of each soil column to maintain a homogenous surface during the leaching event. In a preliminary experiment, two soil columns were saturated with distilled water to obtain moisture content of the soil column of 100% of the field capacity. The difference between the weight of the saturated soil column and its dry weight gave a value of 57 ml for 1 pore volume. The columns were treated with 5 pore volumes of a 0.01M $Ca(NO_3)_2$ solution followed by 1 pore volume of distilled water before spraying 10 ml of the commercial and clay-micelle formulations of SFM at a 420 g/ha$^{-1}$ dose. Distilled water equivalent to half volume pore of the soil column was added every 24 h at the top of the column and the leachate was collected and analyzed for presence of SFM. The same procedure was repeated for 20 days. The leaching experiments were repeated twice for each formulation.

The release of SFZ from organo-clay and commercial formulations was measured in Rehovot sandy soil. Thin layers (50 g) were placed in funnels in which the bottom was covered by Whatman #41 filters. The formulations were mixed with water and the suspensions were transferred to the soil using syringe; then soil samples were covered by Whatman #41 filter papers. The formulations contained 10 mg of active ingredient per each funnel. Soils were washed by water 10 times with 10 min. intervals; the volume of each washing was 35 ml. Effluents of each washing were collected and the concentrations of SFZ were measured.

Figure 2:
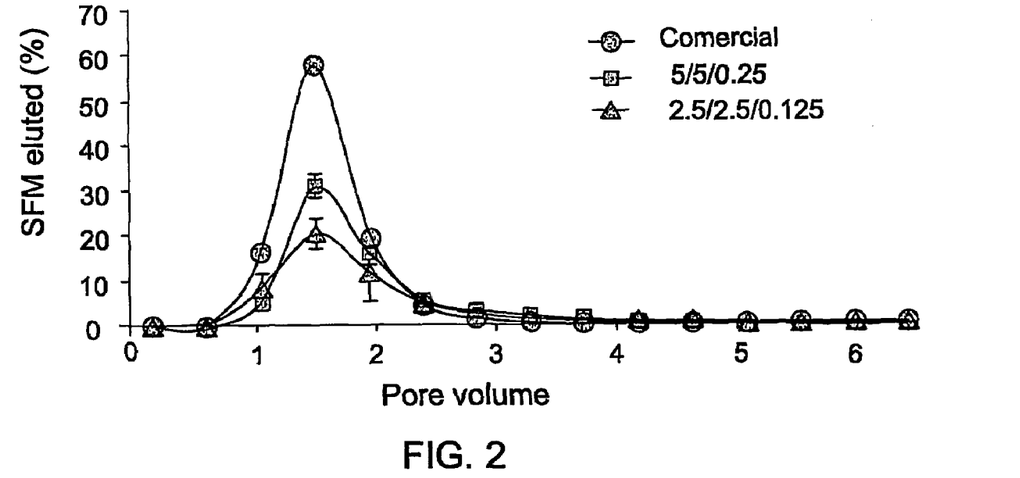
FIG. 2 shows a comparison of the amount of sulfometuron (SFM) eluted for the commercial and the micelle-clay formulations.

Turning to FIG. 2 there are shown the elution curves of the commercial water dispersible-granules formulation (OUST™) and clay-based formulations of SFM-ODTMA. The total recovery percent of SFM from the commercial formulation amounts to 99.2±0.3%, which is in agreement with previous studies indicating low adsorption of sulfonylureas in most agricultural soils, due to their presence as ionic forms (pH>6) and as a result their minimal adsorption on soil colloids (Harvey et al. 1985). Though an increase in the organic matter content improves their adsorption properties to soils, the organic mater content of the soil used (0.92%) is typical for most of the agricultural soils used in Mediterranean areas, indicating a high leaching potential in these regions.

When adding 1.5 pore volumes which is equivalent to 121 mm of rain, the cumulative amounts of SFM eluted were 73.8, 35.9 and 28.6% for the commercial formulation, the 5/5/0.25 and the 2.5/2.5/0.125 formulations, respectively, amounting to a 51 and 61% reduction in leaching, respectively. At 5 pore volumes (403 mm rain), where complete leaching of the commercial formulation occurred, the total leaching percents were 64.6±7.4% and 50.5±5.2% for the 5/5/0.25 and 2.5/2.5/0.125 formulations, respectively. Thus even under terms reflecting high amounts of irrigation, the herbicidal formulations of the present invention leached far less than with the commercial formulation.

Figure 3:
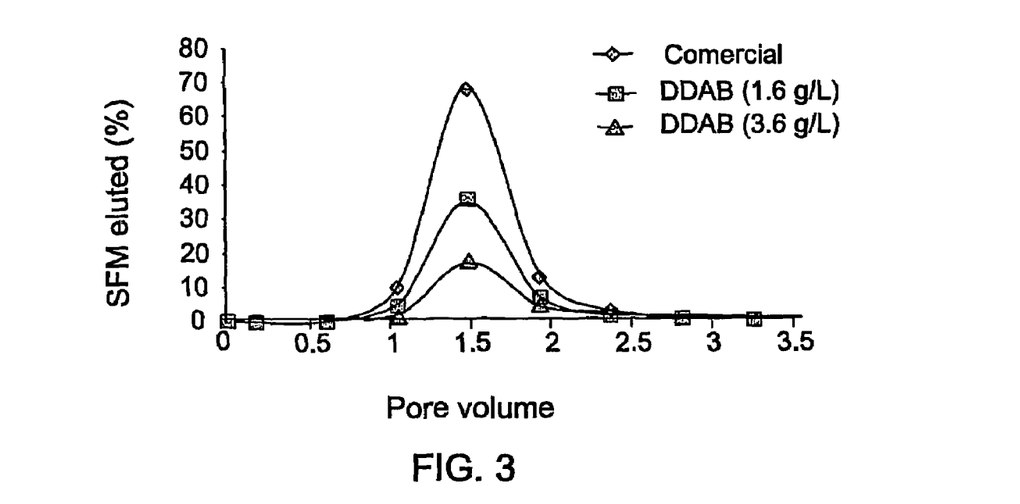
FIG. 3 shows a comparison of the amount of sulfometuron (SFM) eluted for the commercial and the vesicle-clay formulations.
Figure 4:
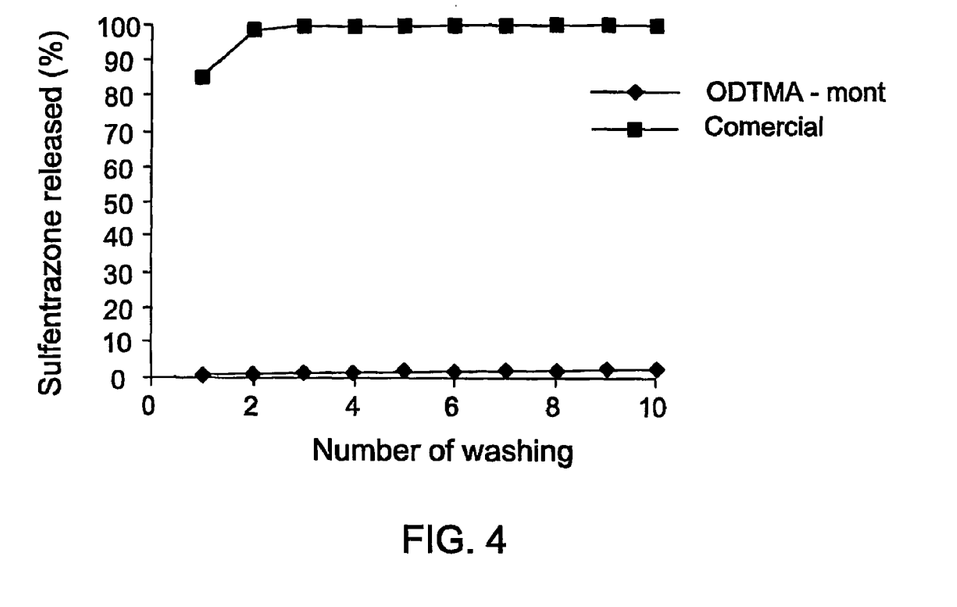
FIG. 4 shows sulfentrazone (SFZ) release from SFZ micelle-clay formulations and a commercial formulation through a thin soil layer.
Figure 5:
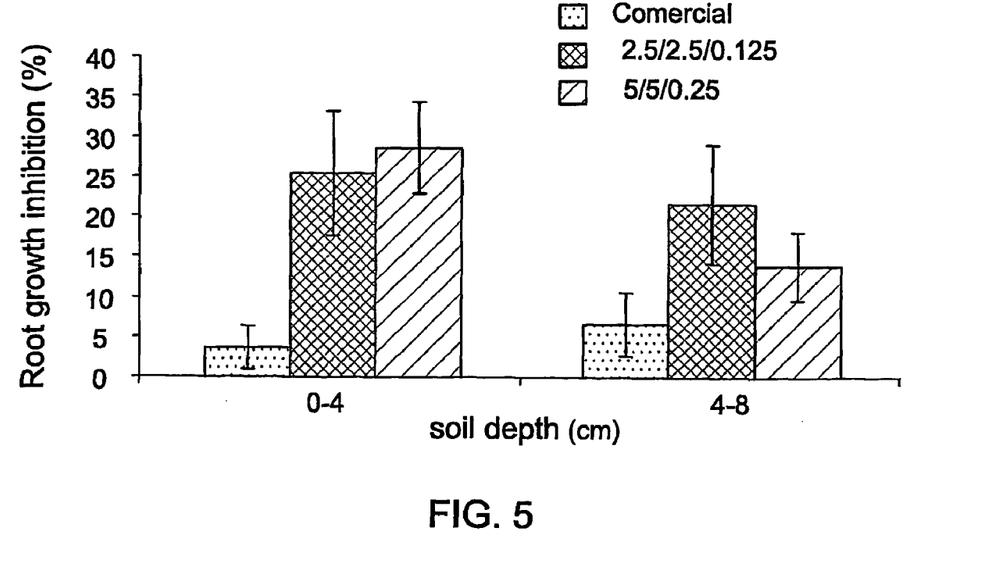
FIG. 5 shows the root growth inhibition of sorghum in the presence of various SFM formulations (column experiment Seville soil).

Turning to FIG. 3 there are described elution curves for the commercial water dispersible-granules formulation (OUST™) and SFM adsorbed in a DDAB-montmorillonite formulation, for two clay concentrations, 1.6 g/L and 3.6 g/L. The elution curves are a result of adding 1.45 pore volume to the soil columns which yield maximal desorbed percent of SFM. The total desorption percentages of SFM were 95%, 49% and 26% of the total amount applied for the commercial, 1.6 g/L and 3.6 g/L DDAB-clay formulations, respectively. This amounts to 48% and 73% reduction in leaching for the 1.6 g/L and 3.6 g/L—clay formulations compared to the commercial formulation. The amount of desorbed SFM from the 3.6 g/L clay formulation is 1.5-fold lower than that from the 1.6 g/L clay formulation, in agreement with the data presented above that a lower desorption occurs for higher clay concentrations. Results of amount of desorbed SFM at different pore volumes for the two clay formulations compared with the commercial formulation are presented in Table 4.

TABLE 4

Percentage of SFM leaching from soil columns as function of added pore volume.

| Cumulative pore volume added | Commercial formulation | DDAB & 1.6 g/L clay | DDAB & 3.6 g/L clay |
|---|---|---|---|
| | | SFM Leached (%) | |
| 0 | 0 | 0 | 0 |
| 0.175 | 0 | 0 | 0 |
| 0.614 | 0 | 0 | 0 |
| 1.053 | 10 | 4.6 | 1.7 |
| 1.491 | 68.7 | 35.8 | 17.5 |
| 1.93 | 12.9 | 6.8 | 4.8 |
| 2.368 | 2.7 | 1.4 | 1.7 |

TABLE 4-continued

Percentage of SFM leaching from soil columns as function of added pore volume.

Figure 6A:
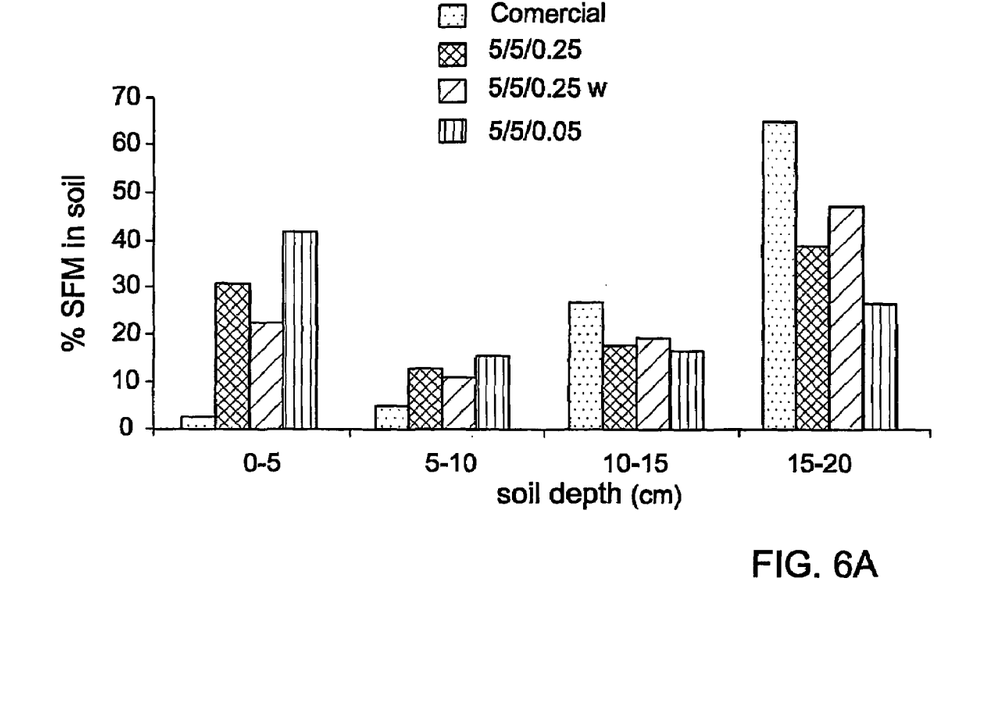
FIGS. 6A and 6B show distribution of sulfometuron (SFM) in soil as a function of its formulation (column experiment Rehovot soil).
Figure 6B:
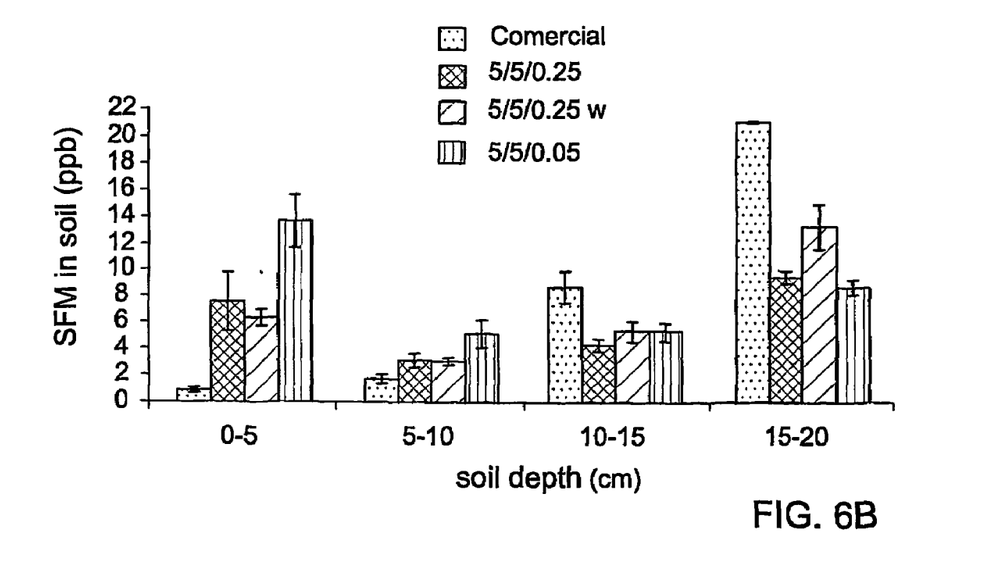

| Cumulative pore volume added | Commercial formulation | DDAB & 1.6 g/L clay | DDAB & 3.6 g/L clay |
|---|---|---|---|
| | | SFM Leached (%) | |
| 2.807 | 0.6 | 0.4 | 0.4 |
| 3.246 | 0 | 0 | 0 |
| 3.684 | 0 | 0 | 0 |
| 4.122 | 0 | 0 | 0 |
| 4.561 | 0 | 0 | 0 |

The overall amount of added water to the columns per day was equivalent to irrigation of 354 $m^3$/ha, (35.4 mm rain). However, the reduction in leaching from the herbicidal formulations of the present invention compared to that occurring from the commercial formulation (OUST™) should be measured at the elution peak, 1.5 pore volume. Although this is a small amount of added water compared to the total amount of added water, it, however, more accurately represents the conditions at the field. Thus for 1.5 pore volume, the cumulative percentages of SFM that leached (the sum of the first 5 rows in Table 4) are 78.7, 40.4 and 19.2 for the commercial formulation, 1.6 g/L and 3.6 g/L —clay-vesicle formulations, respectively. Combining the release profile of the herbicide-vesicle-clay formulation (Table 3) and the leaching results reveals that SFM-DDAB-montmorillonite formulation of 3.6 g/L significantly reduces leaching of SFM to deeper soils.

Turning to FIG. 4 there it presented the release of sulfentrazone from formulations in a thin layer of soil. Release of sulfentrazone from ODTMA-montmorillonite formulations in a thin layer of soil was also small: after one wash only 0.41% of sulfentrazone was released, after 10 washings 2.6% of herbicide were released. For the commercial formulation 85.4% of SFZ were released after first washing, 99.9% were released after 6 washings and 100% was released after 10 washings.

Example 7

Plant Bioassay

Sorghum (HaZera, Israel) was used as a test plant for measuring efficacy of the herbicidal formulation in the two soils described in Example 6.

A. Soil originating from Seville, Spain: After 20 days each soil column (used in the analytical test) was separated into six 4 cm-segments and the soil was dried at 40° C. A bioassay was used to calculate the residual activity of SFM along the length of the soil column by measuring the root inhibition of sorghum seedlings. 5 g of soil from each segment were thoroughly mixed with 60 g of soil and kept after addition of 14 ml of water under darkness in petri dishes, where 9 seeds of sorghum were planted per dish. The petri dishes were kept tilted at an angle of 60° and after 6 days, the elongation of the seedlings was measured. The inhibition percent was calculated as the reduction in the elongation of the seedlings in comparison to those in non-treated soil.

B. Soil originating from Rehovot, Israel: Tin columns, with an upper exposed surface of 100 $cm^2$ and 25 cm long, were 20 cm filled with a sandy loam soil. The column surface was sprayed with the SFM-micelles-clay formulations, the commercial formulation and with water (control) at a rate of 0.1–2 g ai/ha. The columns were carefully irrigated with 500 $m^3$ water/ha (a total of 500 ml per column), adding 50 ml every 20 min. This irrigation level was selected to ensure water movement up to 20 cm depth. The columns were left for 24 h for equilibration and then sliced along their length to obtain two pots.

Each pot was sliced into segments representing different soil depth. Three to four petri dishes were filled with the soil from each slice. In order to stay in the range of sensitivity (0.1–2 ppb) of the plants the three lower slices, 5–10 cm, 10–15 cm and 15–20 cm, were diluted 5, 10 and 20 times, respectively. Samples from the top 5 cm were not diluted or diluted 10 times. The slices were diluted by mixing them with the relevant amount of soil. Five seeds of sorghum were placed on the soil in each petri-dish. The plates were sealed. After six days, the root lengths were measured. The percent of root growth inhibition was calculated by comparing the root length of each sample to the average length of the roots from the control columns. A calibration curve (root length versus SFM concentration) was calculated by using petri dishes with known amounts of SFM (0–5 ppb). The calibration curve for this experiment was: Root length (cm)= 0.4+5.66 exp(−2C). Where C is the concentration ppb) of the herbicide in the soil. The amount of SPM in each unknown sample was calculated by using this calibration curve.

Turning to FIG. 5 there is described the herbicidal activity of SFM formulations at the top of the soil columns (Seville) by way of measuring root growth inhibition of sorghum seeds. The herbicidal activity of the commercial formulation (OUST™) was very low at depths of 0–4 and 4–8 cm, just 3.4% and 6.5% inhibition, respectively. The root growth inhibition measured when applying the clay-micelle formulations was 7.5–8 times higher than that measured for the commercial formulation, which is in agreement with the analytical tests. It should be noted that the soil columns were excessively irrigated, 5 pore volumes, which amounts to 403 mm rain. The combined results of the breakthrough curves and bioassays in Seville soil indicate that the micelle-clay formulations yield a very significant reduction in SFM leaching. Consequently they also yield significantly better herbicidal activity at the top of the soil since a very effective amount of herbicide is maintained at these levels.

Turning to the soil originated from Rehovot, Israel, Three micelle-clay formulations of SFM, 5/5/0.25, 5/1/0.25w, 5/5/0.05 (Table 1) and a commercial formulation (OUST™), were tested using the plant bioassay in soil columns. Four depths of the soil columns were considered for estimating SFM amounts; the top 5 cm, 5–10 cm, 10–15 cm and the deepest segment 15–20 cm. Root growth inhibition of the test plant (sorghum), placed in the soil in the petri-plates was measured. By using a calibration curve of root length as a function of herbicide concentration in the soil ($R^2$=0.993) we calculated the herbicide concentration at each depth (the four slices), and the amount of SFM in each fraction was estimated. A comparison of the sum of the amounts of SFM in the slices with the amount of SFM sprayed on each column gave reasonably good mass balance (80 to 95%), indicating that essentially no SFM from the formulations leached out of the columns. Formulation 5/5/0.25 was sprayed at two different doses of 2 and 0.1 g ai/ha. There was no root growth inhibition when applying 0.1 g ai/ha, implicating that this dose is too low for achieving herbicidal activity.

Turning to FIG. 6A there is presented a comparison of leaching of herbicide into soil layers in different formulations. The commercial formulation (water dispersible-granules, OUST™, Du-Pont, USA) does not adequately fulfill agricultural and environmental basic requirements as can be seen by the distribution of SFM in the soil. Only 2.6% of the applied commercial formulation were detected at the top 5 cm of the soil, and 65.0% were detected at a depth of 15–20 cm. Such a distribution of herbicide throughout the soil depth is certainly undesired. Contrary to the distribution resulting from the water dispersible-granules formulation, a high percent (41.5%) of SFM applied as a micelle-clay formulation, 5/5/0.05, was detected at the top 5 cm of soil and only 26.5% leached to a depth of 15–20 cm. Formulations 5/5/0.25 and 5/5/0.25 w also showed better distribution in the soil in comparison with the commercial formulation. FIG. 6B demonstrates that there are no significant differences in the detected concentrations of SFM, at the different soil depth, between formulations 5/5/0.25 and 5/5/0.25-w. Due to the low desorption of SFM, when applying pre-washing to the 5/5/0.25 formulation, there is no significant difference between the two formulations (Table 1) and their activity in the soil should be similar. FIG. 6B further reveals that the concentrations of SFM released from formulation 5/5/0.05 and detected in the different soil depths are significantly different from those found for the water dispersible-granules formulation. The concentration of SFM that leached from the water dispersible-granules formulation and was detected at a depth of 15–20 cm is more than twice as high as the concentration detected in the soil treated with the micelle-clay formulation, at this soil depth. Thus, use of the herbicidal formulation of the present invention reduces herbicide leaching to harmful depths. Furthermore, in FIG. 6B it is demonstrated that the concentration of SFM released from the formulation 5/5/0.05 and detected in the top 5 cm of the soil is 15 times higher than that found for the water dispersible-granules formulation. Also at a depth of 5–10 cm, there is a significant higher concentration of SFM in the case of the micelle-clay formulations compared to the water dispersible-granules formulation.

Figure 7:
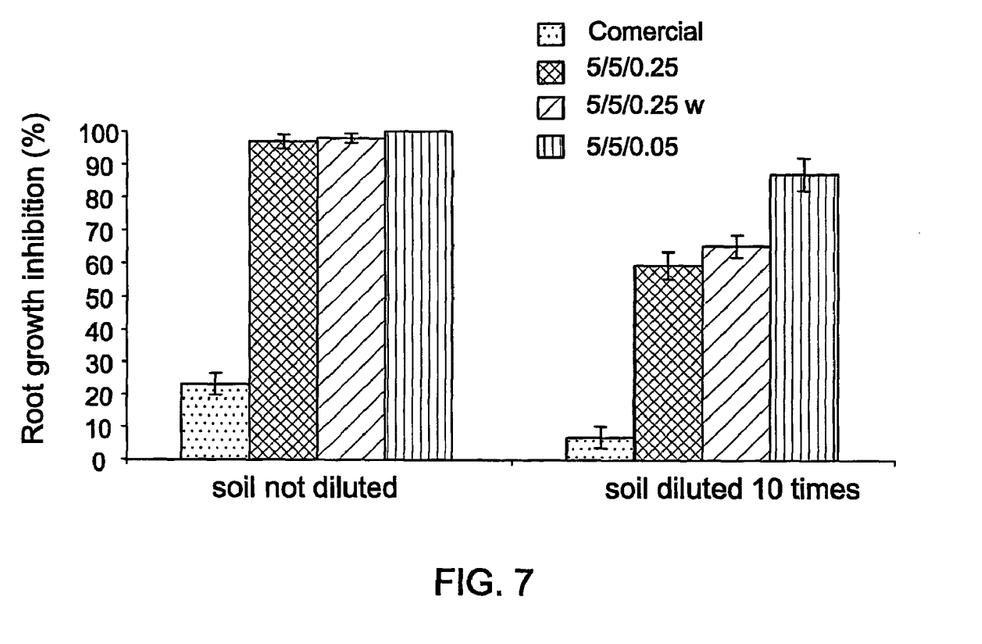
FIG. 7 shows the root growth inhibition of sorghum in the presence of various sulfometuron (SFM) formulations (column experiment Rehovot soil; soil depth 0–5 cm).

Turning to FIG. 7 there is demonstrated efficiency of inhibition of root growth among various herbicidal formulations. The micelle-clay formulations of the present invention yielded close to 100% root growth inhibition at the top 5 cm, whereas the water dispersible-granules formulation gave only 23% inhibition. Diluting the active ingredient in the soil by diluting the soil ten times, the clay-micelle formulations still yielded 60–87% root growth inhibition, whereas the water dispersible-granules formulation had hardly an effect, only 7% inhibition. Such a dilution clearly indicates that also in cases where a ten-fold lower dose of the micelle-clay formulation is applied efficient herbicidal activity is maintained. The activity achieved is better than that achieved with the water dispersible-granules formulation at the recommended doses. FIG. 7 further compares the biological activity of two formulations of the present invention, 5/5/0.05 w and 5/1/0.25. The comparison reveals that the 5/5/0.05 formulation yields a better biological activity at the top 5 cm of the soil and gives rise to less leaching compared to the 5/5/0.25 formulation. A plausible explanation is that the weight percent of SFM in formulation 5/5/0.05 is lower than that in the 5/5/0.25 formulation. A higher clay herbicide ratio reduces SFM desorption from the formulation (Table 2a) and enables slower release.

Leaching of herbicides to the depth of 15–20 cm may already be regarded as potentially harmful to underground water. At such depths, the leaching observed when using the 5/5/0.05 formulation is more than twice that of the water dispersible-granules formulation. Even when considering depths below 10 cm, the corresponding fraction is still twice less. Thus combining the results shown in FIGS. 6 and 7 clearly indicates that an application of the micelle-clay formulation of SFM (5/5/0.05) at 10-fold smaller amounts than the recommended rate may reduce amounts of leached SFM 20-fold below those originating from applying the water dispersible-granules formulation, while achieving 3-fold more biological activity of the herbicide at desirable depths. Thus the herbicidal formulation of the present invention gives rise to both economical and environmental benefits by the potential reduction of applied dose of the formulation. The herbicidal formulation of the present invention enables the application of lower doses of the micelle-clay formulation than the recommended doses for the water dispersible-granules formulation, while maintaining good herbicidal activity.

Example 8

Field Experiment

Figure 8:
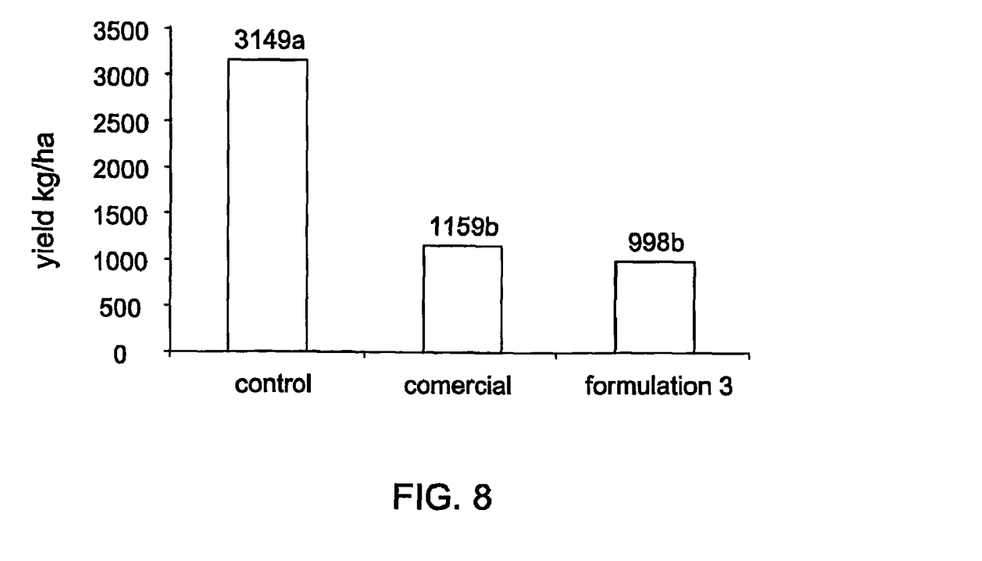
FIG. 8 shows results of growth inhibition in a field experiment employing sulfometuron (SFM) formulations.

A field experiment was conducted to compare and test the efficiency of various SFM formulations. Sorghum seeds were sown in Rehovot sandy soil. On the following day, two SFM formulations were applied, a commercial formulation (water dispersible-granules OUST™, 75% ai), and the micelle-clay formulations in a randomized block design with 4 replications. The SFM rates of the formulations were: 11.6 g/ha in the formulation of the present invention (with ai content only 0.3%), and the commercial formulation was applied at 22.6 g/ha. A few hours after spraying, the field was sprinkler irrigated (50 mm). Sorghum seedlings emerged 5 days later. The experimental plots were irrigated two weeks later with additional 50 mm. In addition, the plots were irrigated twice a week with 100 mm per irrigation. The total irrigation amount during the one-month period was 220 mm. Sampling of undisturbed soil columns from each plot to a depth of 20 cm was done twice. The first sampling was done after applying the first 50 mm of irrigation and the second sampling was done after 150 mm. At the end of the experiment the plant shoot was harvested and the shoot dry yield was determined (FIG. 8). Although the new formulation applied at 11.6 g/ha had only half of the amount of ai in comparison to the commercial formulation it had the same herbicidal activity in the soil.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

The invention claimed is:

1. A herbicidal formulation comprising a herbicide which is incorporated in a micelle or vesicle, wherein said micelle or vesicle containing herbicide is adsorbed onto clay mineral.

2. The herbicidal formulation according to claim 1, wherein said herbicide is a negatively charged herbicide at pH above 6.

3. The herbicidal composition according to claim 2 wherein the herbicide is selected from the group consisting of sulfonylureas, imidazolinones, aryltriazinones, triazolopyrimidines, and their mixtures.

4. The herbicidal formulation according to claim 1, wherein the micelle consists of a positively charged organic cation having large hydrophobic moieties in its structure.

5. The herbicidal formulation according to claim 4 wherein said positively charged micelle is quaternary amine cation micelle selected from the formula $(CH_3)_3N^+(CH_2)_n—CH_3$, n being from 15 to 20.

6. The herbicidal formulation according to claim 1, wherein the vesicle is positively charged and is chosen from the group consisting of lipids.

7. The herbicidal formulation according to claim 1, wherein the clay mineral is a negatively charged clay selected from smectites.

8. The herbicidal formulation according to claim 1, wherein the vesicle is positively charged and is chosen from the group consisting of lipids.

9. The herbicidal formulation according to claim 1, wherein the clay mineral is a negatively charged clay selected from smectites.

10. A method of efficiently destroying undesirable vegetation by applying to said vegetation or to its vicinity an efficient amount of the herbicidal formulation according to claim 1.

11. A method according to claim 10, wherein the herbicide is selected from the group consisting of sulfonylureas, imidazolinones, triazolopyrimidines, aryltriazinones, and their mixtures.

12. A method of efficiently destroying undesirable vegetation according to claim 11, wherein the herbicidal composition is applied at a rate at which leaching of the herbicide is reduced.

13. A method of efficiently destroying undesirable vegetation according to claim 11, wherein the herbicidal composition is applied at a rate at which contamination of underground water is reduced.

14. The herbicidal formulation according to claim 7, wherein said smectite is selected from montmorillonite or sepiolite.

15. The herbicidal formulation according to claim 9, wherein said smectite is selected from montmorillonite or sepiolite.

* * * * *